(12) United States Patent
Culp, Jr.

(10) Patent No.: US 9,764,173 B2
(45) Date of Patent: Sep. 19, 2017

(54) DEVICE, SYSTEM AND METHOD FOR FIRE PREVENTION IN AN OPERATING ROOM

(71) Applicant: William C Culp, Jr., Holland, TX (US)

(72) Inventor: William C Culp, Jr., Holland, TX (US)

(73) Assignee: SCOTT & WHITE HEALTHCARE, Temple, TX (US)

( * ) Notice: Subject to any disclaimer, the term of this patent is extended or adjusted under 35 U.S.C. 154(b) by 228 days.

(21) Appl. No.: 14/329,664

(22) Filed: Jul. 11, 2014

(65) Prior Publication Data

US 2015/0013999 A1     Jan. 15, 2015

Related U.S. Application Data

(60) Provisional application No. 61/845,048, filed on Jul. 11, 2013.

(51) Int. Cl.
| | |
|---|---|
| *A61B 18/14* | (2006.01) |
| *A62C 3/00* | (2006.01) |
| *A61B 18/04* | (2006.01) |
| *A62C 99/00* | (2010.01) |
| *A61B 18/00* | (2006.01) |

(52) U.S. Cl.
CPC .............. *A62C 3/00* (2013.01); *A61B 18/042* (2013.01); *A61B 18/1402* (2013.01); *A62C 99/0018* (2013.01); *A61B 2018/00017* (2013.01); *A61B 2218/005* (2013.01); *A61B 2218/008* (2013.01)

(58) Field of Classification Search
CPC .... A61B 2218/005; A61B 2018/00011; A61B 2018/00017; A61B 2018/00607; A61B 2018/00617; A61B 2017/32035; A61B 2018/008; A61B 18/042; A61B 18/1402; A61B 2218/002; A61B 2218/008; A61B 2218/007
USPC .......................... 606/41, 42, 45, 49; 239/291
See application file for complete search history.

(56) References Cited

U.S. PATENT DOCUMENTS

| | | | | |
|---|---|---|---|---|
| 4,901,719 | A | * | 2/1990 | Trenconsky ....... A61B 17/3203 219/121.5 |
| 5,217,457 | A | * | 6/1993 | Delahuerga .......... A61B 18/042 606/37 |
| 5,693,044 | A | * | 12/1997 | Cosmescu ............ A61B 18/042 604/35 |
| 6,099,525 | A | * | 8/2000 | Cosmescu .............. A61B 18/00 604/35 |
| 7,083,601 | B1 | * | 8/2006 | Cosmescu .............. A61B 18/14 601/35 |
| 2004/0049248 | A1 | * | 3/2004 | Schonborn ........... A61N 5/0616 607/89 |

(Continued)

*Primary Examiner* — Alexander Valvis
(74) *Attorney, Agent, or Firm* — Benjamin Aaron Adler

(57) ABSTRACT

Provided herein are devices, systems and methods utilizing flow of a medically safe inert gas to prevent fires in operating rooms during electrosurgical procedures. A device is disposed around or proximate to or integrated into the tip of an electrosurgical instrument or tool and is in fluid contact with a source of a medically safe inert gas. The gas is flowed around or envelopes the tip as the electrosurgical instrument or tool is utilized. The presence of the medically safe inert gas displaces oxygen, thereby preventing or suppressing fires that may be ignited by sparks generated during use of the tool.

8 Claims, 4 Drawing Sheets

(56) References Cited

U.S. PATENT DOCUMENTS

| | | | | |
|---|---|---|---|---|
| 2010/0094283 A1* | 4/2010 | Cosmescu | A61B 18/1402 | 606/42 |
| 2013/0090643 A1* | 4/2013 | Williams | A61B 18/042 | 606/40 |
| 2013/0296846 A1* | 11/2013 | Canady | A61B 18/042 | 606/37 |

* cited by examiner

DEVICE, SYSTEM AND METHOD FOR FIRE PREVENTION IN AN OPERATING ROOM

CROSS-REFERENCE TO RELATED APPLICATION

This non-provisional application claims benefit of provisional application U.S. Ser. No. 61/845,048, filed Jul. 11, 2013, the entirety of which is hereby incorporated by reference.

BACKGROUND OF THE INVENTION

Field of the Invention

The present invention relates to the field of fire prevention. More specifically, the present invention relates to a device and method utilizing a steady flow of a medically safe inert gas to prevent fires in an operating room environment.

Description of the Related Art

Recent literature from the Joint Commission, Emergency Care Research Institute (ECRI), American Society of Anesthesiologists, and the Anesthesia Patient Safety Foundation has brought both the frequency and potential harm of operating room (OR) fires to the forefront. Operating room fires are listed as one of the top ten health technology hazards of 2013. It is estimated that between 500-600 operating room fires occur every year.

Due to the threat of liability, lawsuits, and the lack of state laws that require operating room fires to be reported, the true number of operating room fires is probably greater. Since 1985, 1.9% of all anesthesiology claims have been due to operating room fires with a median claim of $120,166. Twenty percent of operating room fires result in serious injury and 1-2% result in patient death. Despite the recent abundance of literature, the percentage of claims from electrosurgery-induced operating room fires has increased by more than two fold from 2000-2009. The increasing frequency of claims and the potential threat of operating room fires make it necessary to examine potential solutions to this problem.

For fire to occur, three sources commonly found in the operative environment must be present, i.e., an oxygen source, an ignition source and a fuel source. In 90% of claims from operating room fires, the ignition source is electrosurgery. Other ignition sources that have been reported to cause operating room fires include $CO_2$ lasers, fiberoptic cables, and faulty operating room equipment. The most common fuel source for operating room fires has been surgical drapes accounting for approximately 81% of OR fire claims.

Another potential fuel source which has received much attention is alcohol-containing preparation solution. Such prep-solutions have been indicated as a potential fuel source in 15% of OR fire claims since 1985. Other potential fuel sources include cotton towels, cotton laparotomy sponges, surgical gowns, and utility drapes. Oxidizing agents are also necessary for fires to occur. The most common oxidant is oxygen gas, often delivered to the patient via facemask or nasal cannula. High concentrations of oxygen given to the patient through an open system such as facemask or nasal cannula have been reported as hazardous, especially in surgeries on the head, neck, or upper chest. Nitrous oxide is another potential oxidizing agent, but has received less attention as more fires result from high oxygen concentrations.

One way to remove the possibility of fire in the operating room is by removing the concentration of oxygen in the environment necessary for all potential fuel sources to ignite. Oxygen indexes, or the minimum concentration of oxygen necessary for a material to support a candle-like flame, of the most common surgical materials have been noted before. The oxygen index of woven cotton towels (17.8) was shown to be lower than both a non-woven cellulose draping (18.5) and a polypropylene draping (22.8). Therefore, woven cotton materials do not require as much oxygen to support an initial flame as other materials in the operating room, making it more likely to ignite. In addition, the flammability characteristics of common surgical materials composed predominantly of cotton or polypropylene have been previously analyzed revealing that cotton laparotomy sponges are the most flammable material in increased oxygen concentrations.

By removing one of the primary elements necessary for initiation of a fire, fire can be prevented. Carbon dioxide is a gas proven to prevent ignition and extinguish fire by displacing oxygen. This inert gas extinguishes fire by displacing the required amount of oxygen for continued combustion. Carbon dioxide is also commonly used in the operative environment to improve surgical visibility.

Thus, there is a recognized need for an effective means of fire prevention in operating rooms. Particularly, the prior art is deficient in a device and system that is affixed to an electrosurgical tool to direct a constant flow of a medically safe gas to a surgical site and the surrounding draped area to prevent ignition by the tool. The present invention fulfills this longstanding need and desire in the art.

SUMMARY OF THE INVENTION

The present invention is directed to a fire prevention device in a electrosurgical procedure. The device, in a modified electrosurgical unit pencil, comprises a substantially cylindrically shaped body with open ends and hollow interior and a gas tubing disposed within the hollow interior. A plurality of buttons are disposed along an exterior surface of the body in electronic communication with the electrosurgical unit pencil and a gas actuator is disposed along the exterior surface of the body in electronic communication with the gas flow valve. A gas sleeve is fluidly connected to an end of the gas tubing and is in covering relationship to a tip of the pencil. The present invention is directed to a related device further comprising a source of medically safe inert gas fluidly connected to the gas tubing.

The present invention also is directed to a fire prevention device for an electrosurgical procedure. This device comprises a barrel portion that is disposed around a tip of an electrosurgical tool and a gas inflow port connected to the barrel portion. A gas tubing is disposed along an exterior surface of the electrosurgical tool and into the barrel portion through the gas inflow port. A gas sleeve is attached to the barrel portion in a covering relationship to the tip of the electrosurgical tool and has an orifice and a plurality of ports disposed therethrough fluidly connected to the gas tubing in the barrel portion. A gas flow valve is fluidly connected to the gas tubing.

The present invention is directed further to a fire prevention system for use in an operating room. The fire prevention system comprises either one of the devices as described herein, a source of a medically safe inert gas and a fire extinguisher in fluid contact with the device to prevent and/or suppress operating room fires that may be triggered by the electrosurgical unit pencil.

The present invention is directed further still to a method for to prevent or to suppress a fire during a surgical procedure on a subject in an operating theater. The method comprises positioning a tip of the modified electrosurgical unit pencil or electrosurgical tool, as described herein, on the subject. A flow of a medically safe inert gas is activated through the gas sleeve comprising the device to generate a shield of the medically safe inert gas around the tip during the surgical procedure.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
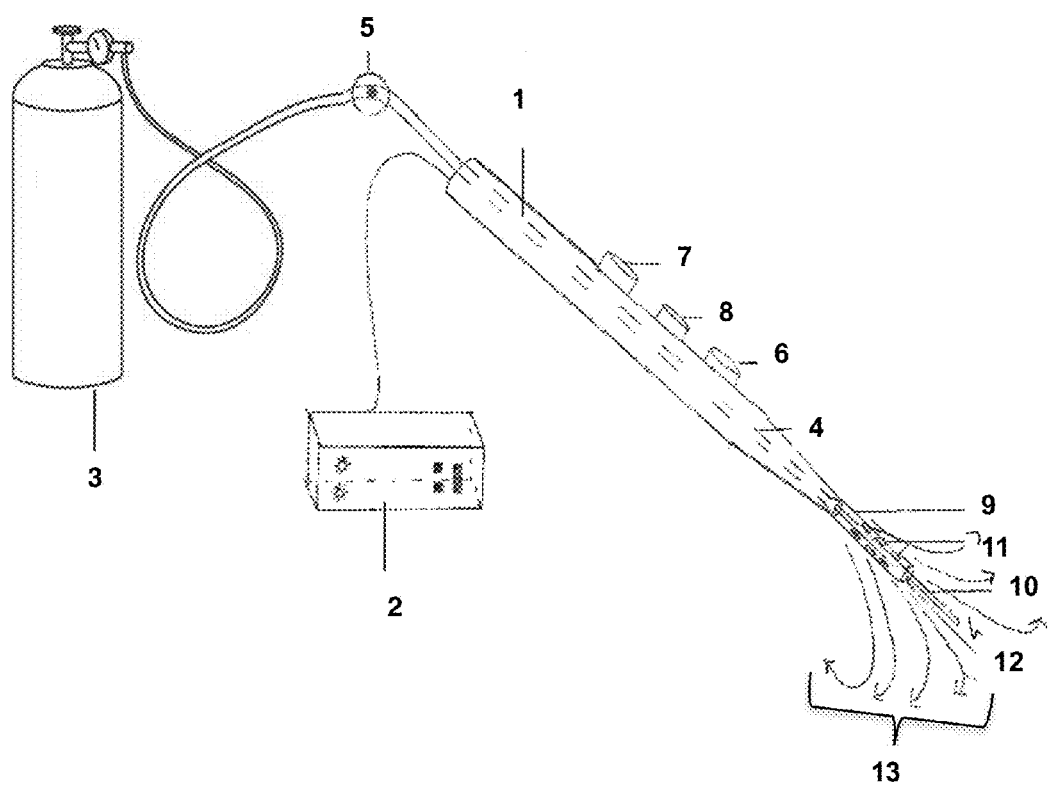
FIG. 1 is a schematic diagram demonstrating an electrosurgical unit pencil, its attachment to a source of a medically safe inert gas, its connection to an electrosurgical unit generator, and a general view of the electrosurgery inert gas shield fire prevention/suppression device.

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "medically safe inert gas" refers to any gas that is not necessarily hazardous for human health and does not combust with any flammable gas, liquid or other objects in an operating room.

As used herein, the term "subject" refers to any human or animal upon which the electrosurgical procedure is performed.

In one embodiment of the present invention, there is provided fire prevention device for an electrosurgical procedure, comprising, in a modified electrosurgical unit pencil, a body having a substantially cylindrical shape with open ends and a hollow interior; a gas tubing disposed within the hollow interior; a gas flow valve fluidly connected to the gas tubing; a plurality of buttons disposed along an exterior surface of said body in electronic communication with the electrosurgical unit pencil; a gas actuator disposed along the exterior surface of said body in electronic communication with the gas flow valve; and a gas sleeve fluidly connected to an end of the gas tubing and in a covering relationship to a tip of the pencil.

Further to this embodiment, the device may comprise a source of medically safe inert gas fluidly connected to the gas tubing. The medically safe inert gas may be carbon dioxide, nitrogen or helium or a combination thereof. In both embodiments, the gas actuator may be a manual gas flow trigger. Also, the plurality of buttons may be manual cut or coagulate triggers for the electrosurgical unit pencil.

Also in both embodiments, the gas sleeve may have a substantially cylindrical shape, covering about 20% to about 50% of the length of the tip of the electrosurgical unit pencil. In addition, the gas sleeve may have an orifice at a distal end thereof disposed around the electrosurgical unit pencil tip. Furthermore, the gas sleeve may comprises a plurality of gas ports each disposed at an angle through a surface thereof. As such, a combination of the gas flowing through the ports and orifice may form a fire suppressant gas shield disposed around the tip of the pencil. The gas shield has a substantially conical shape with a radius of about 2 cm to about 3 cm and a length about 2 cm to about 4 cm.

In another embodiment of the invention, there is provided a fire prevention system for the use in an operating room comprising the device in a modified electrosurgical unit pencil, as described supra, a source of medically safe inert gas, and a fire extinguisher.

In yet another embodiment of the invention there is provided a method to prevent or to suppress a fire during a surgical procedure on a subject in an operating theater, comprising the steps of positioning a tip of the modified electrosurgical unit pencil, as described supra, on the subject, and activating the flow of a medically safe inert gas through the gas sleeve comprising the device to generate a shield of the medically safe inert gas around the tip during the surgical procedure.

In yet another embodiment of the invention, there is provided a fire prevention device for an electrosurgical procedure comprising a barrel portion disposed around a tip of an electrosurgical tool, a gas inflow port connected to the barrel portion, a gas tubing disposed along an exterior surface of the electrosurgical tool and into the barrel portion through the gas inflow port, a gas sleeve attached to the barrel portion in a covering relationship to the tip of the electrosurgical tool and having an orifice and a plurality of ports disposed therethrough fluidly connected to the gas tubing in the barrel portion and a gas flow valve fluidly connected to the gas tubing.

Further to this embodiment, the device may comprise a source of medically safe inert gas fluidly connected to the gas tubing. The medically safe inert gas may be carbon dioxide, nitrogen or helium or a combination thereof. In another further embodiment, the may comprise means for securing device to the electrosurgical tool comprising an attachment band, tension straps, or hook and loop attachments.

In all embodiments a combination of the gas flowing through the ports and the orifice may form a fire suppressant gas shield disposed around the tip of the electrosurgical tool. Also, the gas shield may have a substantially conical shape with a radius of about 2 cm to about 3 cm and a length about 2 cm to about 4 cm.

In yet another embodiment of the present invention, there is provided a fire prevention system for the use in an operating room comprising the device secured to an electrosurgical tool, as described supra, a source of medically safe inert gas, and a fire extinguisher.

In yet another embodiment of the present invention, there is provided a method to prevent or to suppress a fire during a surgical procedure on a subject in an operating theater, comprising the steps of attaching the device, as described supra, to an electrosurgical tool, positioning a tip of the electrosurgical tool attached to the device on the subject, and activating the flow of a medically safe inert gas through the gas sleeve comprising the device to generate a shield of said medically safe inert gas around the tip during the surgical procedure.

Provided herein are devices, systems and methods utilizing delivery of an inert gas during an electrosurgical procedure for fire prevention and suppression. The fire suppression device may be integrated within an electrosurgical tool or may be an attachment or accessory to an existing or unmodified electrosurgical tools. For example, the electrosurgical tool may be an electrosurgical unit pencil.

The system comprises a device that attaches to an electrosurgical pencil or other tool and covers or substantially covers the tip. A medically safe inert gas is propelled towards the electrosurgical unit (ESU) pencil tip or delivered through a plurality of ports disposed around the tip to produce a gas shield around the tip. The positioning of the device enables a directed flow of gas that flows with the tip as the tip is moved during a surgical procedure. A medically safe inert gas cone around the area of electrosurgical application is an effective means of lowering the risk of operating room fires. The flow rate may be in the range of 2 L/min to 10 L/min. The flow rate may be constant or varied by the operator using the manual actuator. In order to be an effective fire preventative, enough medically safe inert gas must surround the surgical site to displace the concentration of oxygen necessary for ignition. Therefore, the flow rate of the medically safe inert gas, the oxygen concentration of the surgical environment, and the shape and placement of the device are important variables that affect the ability of the medically safe inert gas to prevent ignition of surgical materials in the operating room. The device configuration is effective to alleviate gas pressure to prevent embolism and damage to patient tissue and to increase the fire prevention area.

Particularly, the device comprises a means for delivering a flow, for example, pipes, delivers or flows, of a medically safe inert gas through a sleeve or gas sleeve in fluid connection with the source of the inert gas that overlays the tip of the electrosurgical tool. This sleeve has multiple ports and an open orifice at the pencil tip which direct the medically safe inert gas around the spark-producing pencil tip. The ports may include collar ports and sleeve ports. The device exploits the fire extinguishing characteristics of gases such as carbon dioxide, nitrogen or helium by creating a shield of medically safe inert gas along the sides and end of the electrosurgical tool, such as, a tip of an electrosurgical unit pencil. This substantially conical shield envelops the active portion of the tool tip, thereby covering the electrical spark and creating a micro-atmosphere that minimizes the presence of oxygen. In so doing, the risk of fire is greatly reduced while still permitting normal function of the electrosurgical unit. Additionally, the conical shield of the medically safe inert gas enhances the surgeon's visualization of tissues by blowing away blood and debris.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

FIG. 1 depicts the invention, which is a modification of a standard electrosurgical unit pencil 1. This pencil is connected to a standard electrosurgical unit generator 2. A source of a medically safe inert gas 3 is connected to the electrosurgical unit pencil, and in one embodiment, flows through gas tubing 4 integrated or disposed within the hollow interior of the body of the pencil 1. A gas flow valve 5 is fluidly connected the gas tubing and controls carbon dioxide or other gas flow during use. This valve could either be operated manually, or could be designed to trigger gas flow prior to electrical current exiting the pencil 1. The pencil 1 has standard use buttons for activating the "cut" 6 and "coagulate" 7 features in electronic communication with the electrosurgical unit pencil and disposed along the exterior surface of the pencil. The pencil also may have a gas actuator 8. This actuator is used to manually trigger the flow of the medically safe inert gas through the pencil 1. A cylindrical gas sleeve 9 covers most of the length of the electrosurgical unit pencil tip 10. This sleeve is fluidly connected to the gas tubing 4. The sleeve has a distal orifice 12 that opens around the pencil tip 10 and multiple ports 11 that are shaped and angled to form a gas shield 13 of medically safe inert gas when the gas exits the pencil 1, preventing fire at the pencil tip 10. It is important to note that sparks can leave the pencil tip at any non-insulated region, stressing the value of a large, complete conical shield of the medically safe gas to maximize its fire protective qualities and efficacy.

Figure 2:
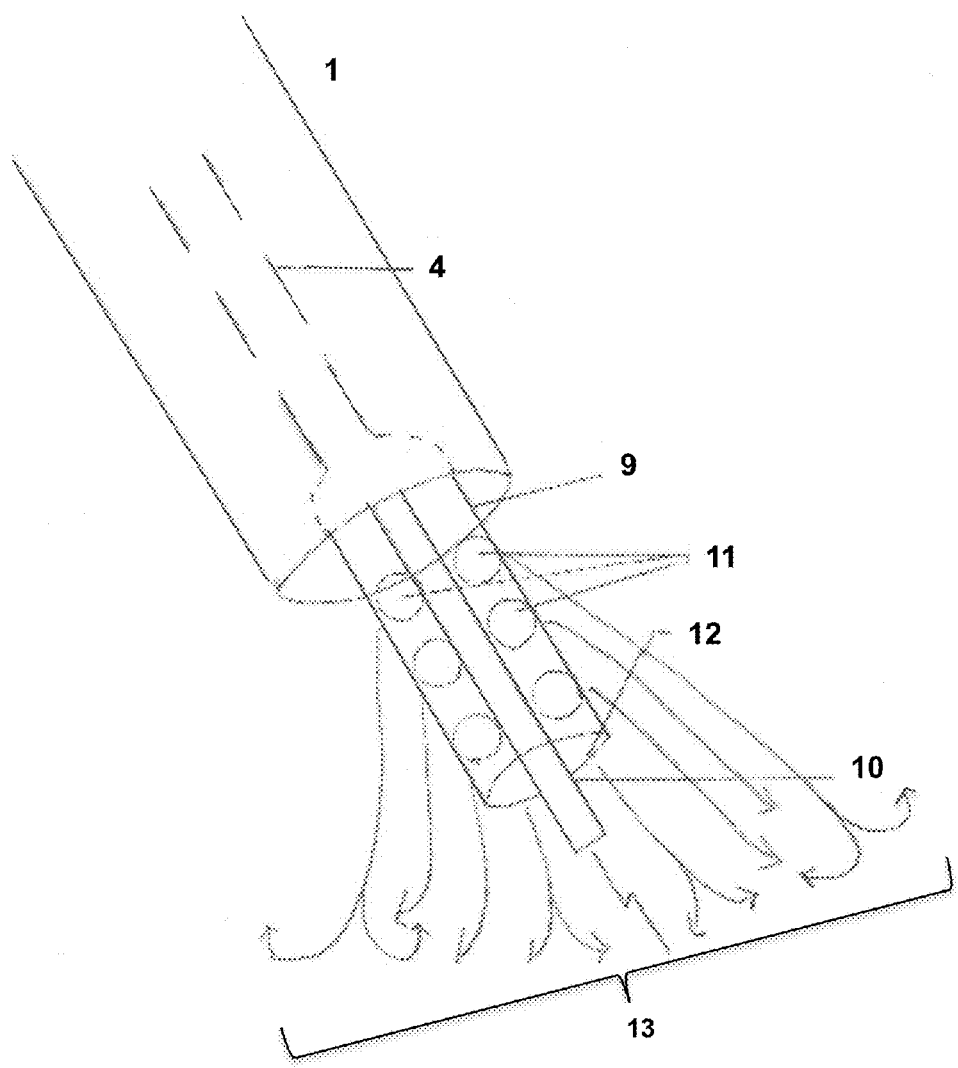
FIG. 2 is a magnified view of the end of the electrosurgical unit pencil end, depicting the gas sleeve ports and orifice, and the resultant shield of carbon dioxide as it envelops the active portion of the electrosurgical unit pencil tip.

FIG. 2 shows a magnified view of certain portions of the device. Here, the pathway of the medically safe inert gas can be traced as it flows through the gas tubing 4, into the gas sleeve 9, and through the various precisely sized and angled gas sleeve ports 11 and the gas sleeve orifice 12. This arrangement of ports and orifice allows the creation of a conical shield of the medically safe gas that then covers the active portions of the electrosurgical unit pencil tip 10. This shield 13 effectively reduces the oxygen concentration at the pencil tip 10, reducing the possibility of fire by replacing oxygen with a fire suppressant and/or a medically safe inert gas.

Figure 3A:
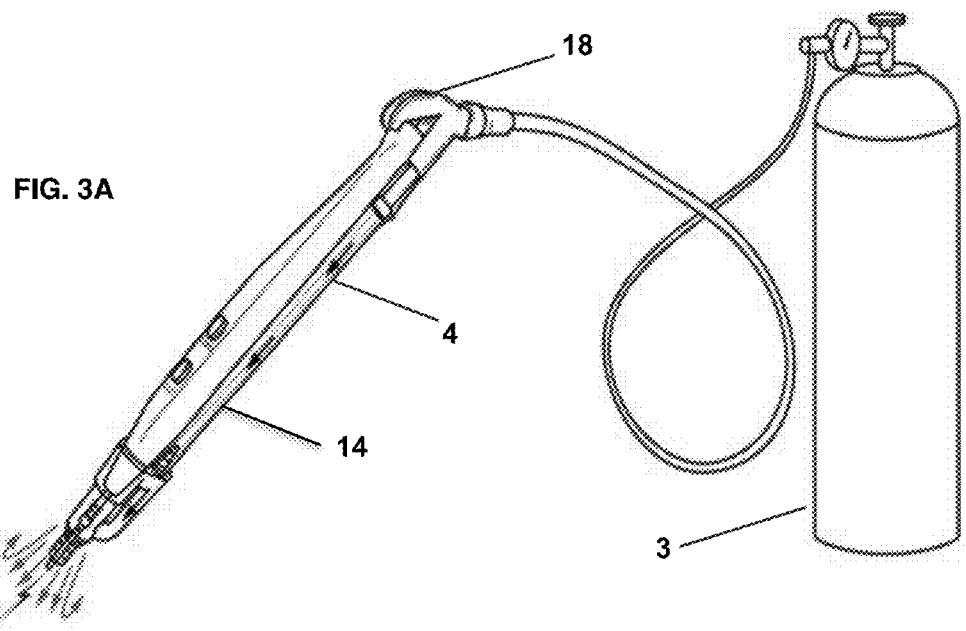
FIG. 3A illustrates an alternate embodiment of the invention which can be added as an accessory to an existing electrosurgical tool. This view depicts the attachment band.
Figure 3B:
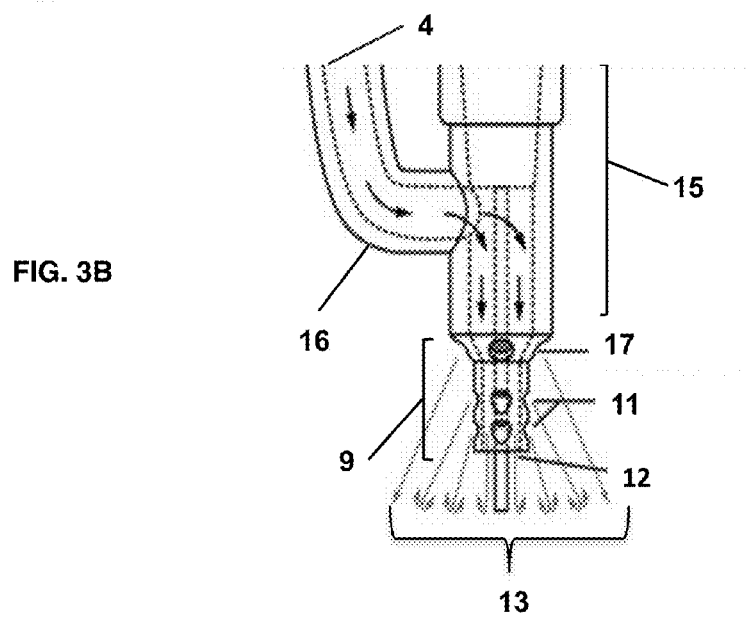
FIG. 3B is a magnified view and shows the gas sleeve ports, collar ports and orifice that can slide over an electrosurgical unit pencil.

FIGS. 3A-3B depict another embodiment of the device that may be attached as an accessory to the body 14 of an existing electrosurgical unit pencil. Instead of modifying a traditional electrosurgical unit pencil, the invention may be placed over the end of the pencil assembly using a means for securing the device 18, such as, but not limited to an attachment band, tension straps, or a hook and loop attachments or other mechanism known in the art to secure the device to body 14 of the pencil. The device comprises three sections: a barrel portion 15 that is disposed around a tip 14 of the electrosurgical tool, a gas inflow port 16 to receive the gas tubing 4 through which a medically safe inert gas enters is connected to the barrel portion, a gas sleeve 9 that is attached to the barrel portion in a covering relationship to the tip of the electrosurgical tool. The gas sleeve has an orifice 12 and a plurality of ports 11 disposed therethrough fluidly connected to the gas tubing in the barrel portion. A gas flow valve 5 (see FIG. 1) is fluidly connected to the gas tubing. A medically safe inert gas can thereby flow into the gas sleeve 9 via externally attached gas tubing 4. The medically safe inert gas then exits the gas sleeve 9 via the sleeve ports 11, sleeve orifice 12 and collar ports 17. This creates a cone-shaped shield 13 of protective medically safe inert gas at the area of the electrosurgical unit pencil tip 10, as described above. Furthermore, an electronic interlock to initiate gas flow just before sending electric current through the electrosurgical tool may be added to allow carbon dioxide flow only when needed. For example, similar to the plurality of buttons 6,7 to activate the cut and coagulate features of the tool that are in electronic communication with the modified electrosurgical unit pencil, the electrosurgical tool may comprise the interlock.

The following example(s) are given for the purpose of illustrating various embodiments of the invention and are not meant to limit the present invention in any fashion.

EXAMPLE 1

Materials and Methods
Testing Set-Up

A prototype device described supra was created using a low-viscosity, heat resistant, liquid photopolymer, comprising the following 3 sections: a barrel portion that mates the device to the electrosurgical unit pencil; a gas inflow port through which carbon dioxide enters the device; and a sleeve that covers the proximal portion of the pencil tip but leaves the distal tip exposed. The sleeve consists of a single main orifice through which the pencil tip and carbon dioxide passes, 8 sleeve ports and 4 collar ports. The sleeve and collar ports were angled such that, when combined with the straight main orifice, the exiting carbon dioxide forms a cone enshrouding the active portion of the pencil tip. The device was attached to an electrosurgical pencil (Valleylab) and used to propel carbon dioxide into the surgical field in a conical shape. The pencil tip extended 1 cm past the device sleeve.

For testing, laparotomy sponges were chosen as the potential fuel source in order to ensure the occurrence of fire every time with the control group and to ensure the efficacy of the fire prevention device since the laparotomy sponge was previously determined to be the most flammable of all materials tested in oxygenated environments. A 8.6×8.6-cm testing swatch is obtained from the laparotomy sponge and placed directly on top of a conductive copper plate. The laparotomy sponge is determined to be the most flammable of several common operating room materials previously tested for flammability. The electrosurgery unit return pad input was connected directly to the copper plate via alligator clips. An electrosurgical unit pencil (E2516, Valleylab, Boulder, Colo.) with stainless steel cutting blade (Ref. 138104, Conmed, Utica, N.Y.) was connected to an electrosurgical unit (Surgmaster UES-40, Olympus, Center Valley, Pa.).

The testing apparatus was placed within a 46 cm by 46 cm by 46 cm testing chamber with transparent walls composed of Plexiglass that provided visibility as well as safety. The ability of carbon dioxide to suppress fire on the laparotomy sponge was then tested at three different oxygen concentrations: 21%, 50%, and 100%. Oxygen was piped into the testing chamber via tubes connected to oxygen tanks. The concentration of oxygen was measured using a multi-gas analyzer (Apollo Anesthesia Workstation, Dräger Medical, Lübeck, Germany). This standard setup was used in all experiments.

Testing conditions are designed to resemble highly flammable scenarios. Instead of using human tissue as the conductive material for the electrosurgical unit, a highly conductive copper plate was used, which allowed for the production of greater sparks, and therefore, a more flammable environment. By having more sparks, fire was generated every time without the presence of carbon dioxide. To further increase the possibility of a fire to occur, the oxygen concentration also was increased to a point beyond normal operating room conditions. However, sparks, laparotomy sponges, and high concentrations of oxygen can be found in the operating room theatre. Oxygen may get trapped underneath surgical drapes while micro sparks are frequently generated by the electrosurgical unit tip.

Ignition of Laparotomy Sponge

The electrosurgical pencil was placed into the testing chamber and continually activated at 50 W cut mode while targeting the laparotomy sponge until the sponge ignited or until 30 seconds elapsed. Five trials were done in each concentration of oxygen both with a flow rate of 10 L/min of carbon dioxide and without the use of carbon dioxide, resulting in a total of thirty tests. Videography was used to measure time to ignition after the electrosurgical pencil was applied to the swatch. Time to ignition was measured as the time between initial contact of the tip of the electrosurgical unit pencil and the time at which a sustainable flame was produced on the laparotomy sponge swatch. After the trials were recorded, each video was reviewed frame by frame to determine the time to ignition (or the time of electrosurgical unit activation if no ignition) of each sample. The difference between the time of the initial contact and the time at which a sustainable flame was produced was calculated three times for each trial. These results were averaged to give the recorded value of time to ignition. Random video recordings were checked for accuracy by the other investigators. The video recording has a temporal resolution of 30 frames per second.

Gas Composition

Electrical current transmission from the electrosurgical unit device is critical for its operation and particular clinical effect (cutting, coagulation, extent of tissue effect, etc.). The amount of current transmitted is related to the pressure of the gas through which the current is conducted, and breakdown voltage. Paschen's Law describes this relationship, stating:

$$V = apd/\ln(pd) + b$$

where V is breakdown voltage, p is pressure, d is gap distance, and a and b are constants related to gas composition. Since our device involves covering the electrosurgical unit tip with carbon dioxide (a gas with different properties than air), current patterns may be altered. Internal preliminary testing shows that the electrosurgical unit functions even in a pure carbon dioxide environment, and calculations suggest about a 15%-20% reduction in current flow.

Paschen's Law is utilized to determine how altering the gas composition around the electrosurgical unit tip affects its function. Specifically, current conduction through the electrosurgical unit is measured via an electric multi-meter connected to a metal plate that serves as a target of the electrosurgical unit pencil. Using low, routine, and high electrosurgical unit current settings in low, high, and 100% carbon dioxide environments, the effect of replacing a nitrogen-based atmosphere with carbon dioxide on the use of the electrosurgical unit is determined.

Statistical Analysis

To assess the consistency of time measurement data, intraobserver and interobserver variabilities were determined. An investigator (B. K.) measured the time of ESU activation twice for each test, and a second investigator (S. L.) measured the time of ESU activation a third time. The Pearson correlation coefficient (r) and the Bland-Altman method for comparing paired measurements were used to examine intraobserver and interobserver variabilities with statistical software (Analyze-it 2.24, Leeds, United Kingdom). To determine the times that should be used in the final data analysis and for all discrepancies between the 3 data sets, both S. L. and B. K. reexamined the videography and agreed upon the most accurate time of ESU activation. These final time measurements composed a fourth data set, from which median and SD were calculated. The Clopper-Pearson exact value test was used to determine confidence intervals. Homogeneous data allowed pooling of data into a 2×2 contingency table for analysis with the 2-tailed Fischer exact testing. $P<0.05$ was deemed statistically significant.

EXAMPLE 2

Ignition Results

Figure 4:
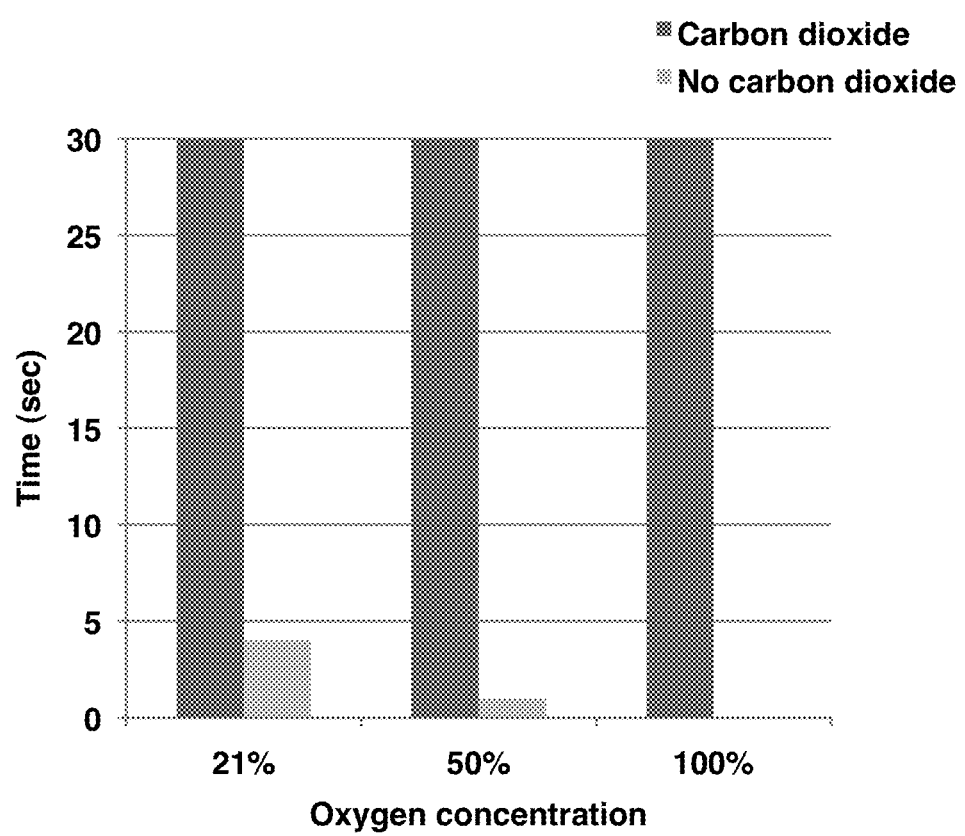
FIG. 4 illustrates the time in seconds before the electrosurgical pencil starts a fire in the presence of 10 L/min carbon dioxide and increasing oxygen concentrations.

In room air, 50% oxygen, and 100% oxygen without the use of the carbon dioxide, the electrosurgical unit created a sustainable flame in each trial (FIG. 4) The median±SD ignition time of the control group in 21% oxygen was 3.0±2.4 seconds, in 50% oxygen 0.1±1.8 seconds, and in 100% oxygen 0.03±0.1 seconds. No fire was observed when the carbon dioxide was applied in all concentrations of oxygen: 21%, 50%, and 100% (0/15 trials; P<0.0001). The 95% confidence interval for the risk of fire for the pooled control group was 82% to 100% and for the fire safety device was 0% to 18%. The exact 95% confidence interval for the absolute reduction in risk of fire was 76% to 100%. Intraobserver and interobserver measurements showed a strong agreement by the Pearson correlation and the Bland-Altman method. The Pearson r coefficients for the intraobserver and interobserver comparisons were 1.0 and 1.0, respectively. Bland-Altman biases (95% limits of agreement) were −0.01 (−0.8 to 0.8) seconds and −0.17 (−1.6 to 1.2) seconds, respectively.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A fire prevention device for an electrosurgical procedure, comprising, in an electrosurgical unit pencil:
   a body having a substantially cylindrical shape with open ends and a hollow interior;
   a gas tubing disposed within the hollow interior;
   a gas flow valve fluidly connected to the gas tubing;
   a plurality of buttons disposed along an exterior surface of said body in electronic communication with the electrosurgical unit pencil, said plurality of buttons including:
      a gas actuator in electronic communication with the gas flow valve; and
   a gas sleeve having an orifice at a distal end thereof comprising plurality of gas ports each disposed at an angle a surface thereof, said gas sleeve fluidly connected to an end of the gas tubing inside of the body and formed at a distal end of the body, the gas sleeve partially covering a tip of the electrosurgical unit pencil;
   a source of medically safe inert gas fluidly connected to the gas tubing; and
   wherein a combination of the medically safe inert gas flowing through said plurality of gas ports and said orifice forms a fire suppressant gas shield around the tip of the electrosurgical unit pencil.

2. The device of claim 1, wherein said medically safe inert gas is carbon dioxide, nitrogen or helium or a combination thereof.

3. The device of claim 1, wherein said gas actuator is a manual gas flow trigger.

4. The device of claim 1, wherein said plurality of buttons are manual cut or coagulate triggers.

5. The device of claim 1, wherein said gas sleeve has a substantially cylindrical shape, covering about 20% to about 50% of a length of the tip of the electrosurgical unit pencil.

6. The device of claim 1, wherein the gas shield has a substantially conical shape with a radius of about 2 cm to about 3 cm and a length about 2 cm to about 4 cm.

7. A fire prevention system for the use in an operating room, comprising:
   the device of claim 1.

8. A method to prevent or to suppress a fire during a surgical procedure on a subject in an operating theater, comprising the steps of:
   positioning the tip of the electrosurgical unit pencil of claim 1 on or near the subject; and
   activating the flow of the medically safe inert gas through the gas sleeve comprising the device to generate the shield of said medically safe inert gas around the tip during the surgical procedure.

* * * * *